US008076361B2

(12) United States Patent
Cotton et al.

(10) Patent No.: US 8,076,361 B2
(45) Date of Patent: Dec. 13, 2011

(54) FORM OF S-OMEPRAZOLE

(75) Inventors: Hanna Cotton, Södertälje (SE); Anders Kronström, Södertälje (SE); Anders Mattson, Södertälje (SE); Eva Möller, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/784,881

(22) Filed: May 21, 2010

(65) Prior Publication Data

US 2011/0130570 A1     Jun. 2, 2011

Related U.S. Application Data

(60) Continuation of application No. 11/853,323, filed on Sep. 11, 2007, now Pat. No. 7,745,466, which is a continuation of application No. 10/672,936, filed on Sep. 25, 2003, now Pat. No. 7,411,070, which is a continuation of application No. 10/076,711, filed on Feb. 14, 2002, now Pat. No. 6,677,455, which is a division of application No. 09/077,719, filed as application No. PCT/SE98/00974 on May 25, 1998, now Pat. No. 6,369,085.

(30) Foreign Application Priority Data

May 30, 1997    (SE) ........................................ 9702065

(51) Int. Cl.
*A61K 31/4439* (2006.01)
*C07D 401/12* (2006.01)
(52) U.S. Cl. ..................................... 514/338; 546/273.7
(58) Field of Classification Search ................ 546/273.7; 514/338
See application file for complete search history.

(56) References Cited

U.S. PATENT DOCUMENTS

| | | | |
|---|---|---|---|
| 4,255,431 A | 3/1981 | Junggren et al. ................ 424/263 |
| 4,738,974 A | 4/1988 | Brändström .................... 514/338 |
| 4,786,505 A | 11/1988 | Lovgren et al. ................ 424/468 |
| 5,204,118 A | 4/1993 | Goldman et al. | |
| 5,244,891 A | 9/1993 | Kaplan et al. | |
| 5,417,980 A | 5/1995 | Goldman et al. | |
| 5,530,160 A | 6/1996 | Nore et al. ..................... 562/571 |
| 5,676,884 A | 10/1997 | Tiers et al. ..................... 252/582 |
| 5,690,960 A | 11/1997 | Bengtsson et al. ............. 514/338 |
| 5,693,818 A * | 12/1997 | Von Unge ................... 546/273.7 |
| 5,714,504 A * | 2/1998 | Lindberg et al. .............. 514/338 |
| 5,817,338 A | 10/1998 | Bergstrand et al. ............ 424/468 |
| 5,840,552 A | 11/1998 | Holt et al. | |
| 5,877,192 A * | 3/1999 | Lindberg et al. .............. 514/338 |
| 5,900,424 A | 5/1999 | Källström et al. ............. 514/338 |
| 5,948,913 A | 9/1999 | Yamamoto et al. | |
| 6,022,985 A | 2/2000 | Authelin et al. | |
| 6,132,771 A | 10/2000 | Depui et al. | |
| 6,136,344 A | 10/2000 | Depui et al. | |
| 6,183,776 B1 | 2/2001 | Depui et al. | |
| 6,365,184 B1 | 4/2002 | Depui et al. | |
| 6,369,085 B1 | 4/2002 | Cotton et al. .................. 514/338 |
| 6,613,354 B2 | 9/2003 | Depui et al. | |
| 6,677,455 B2 | 1/2004 | Kronström et al. | |
| 6,747,155 B2 | 6/2004 | Kronstrom et al. | |
| 7,411,070 B2 | 8/2008 | Cotton et al. | |
| 7,488,497 B2 | 2/2009 | Depui et al. | |
| 7,745,466 B2 * | 6/2010 | Cotton et al. .................. 514/338 |
| 2007/0122470 A1 | 5/2007 | Johansson et al. | |
| 2008/0255363 A1 | 10/2008 | Cotton et al. | |
| 2009/0297594 A1 | 12/2009 | Depui et al. | |

FOREIGN PATENT DOCUMENTS

| | | |
|---|---|---|
| CN | 1136564 | * 11/1996 |
| DE | 4 035 455 | 5/1992 |
| EP | 0005129 | 10/1979 |
| EP | 0124495 | 11/1984 |
| EP | 0247983 | 12/1987 |
| IN | 1344/DEL/98 | 5/1998 |
| WO | 9427988 | 12/1994 |
| WO | 9501977 | 1/1995 |
| WO | 9601623 | 1/1996 |
| WO | 9602535 | 2/1996 |

OTHER PUBLICATIONS

Erlandsson, P. et al. "Resolution of the enantiomers of omeprazole and some of its analogues by liquid chromatography on a trisphenylcarbamoyl cellulose-based stationary phase", Journal of Chromatography, 532 (1990) 305-319.
von Unge, S. et al. "Stereochemical assignment of the enantiomers of omeprazole from X-ray analysis of a fenchyloxylmethyl derivative of (+)-(R)-omenrazole", *Tetrahedron Asymmetry*, vol. 8, No. 12, pp. 1967-1970 (1997).
Japanese Chemical Society, Experimental Chemical Seminar, vol. 18. p. 55 (translation), 1958.
An Introduction to Crystal Chemistry by Evans Cambridge at the Univ. Press, 1964.
Notice of Allegation, filed Nov. 13, 2007, pursuant to the patented Medicines (Notice of Compliance) *Regulations* with respect to Canadian Letters Patent No. 2,290,963.
Rajendra K. Khankari et al., "Pharmaceutical hydrates", Thermochimca Acta 248 (1995) 61-79. Abstract of CN1136564: Aomeilazole salt hydrate for gastric acid inhibitor and its preparing method, Nov. 27, 2006.
Haijian Zhu et al. "Influence of water activity in organic solvent + water mixtures on the nature of the crystallizing drug phase. 1 Theophylline", International Journal of Pharmaceutics 135 (1996) 151-160.
Stephen Byrn et al., "Pharmaceutical Solids: A Strategic Approach to regulatory Consideration", Pharmaceutical Research, vol. 12, No. 7 (1995), 945-954.

* cited by examiner

*Primary Examiner* — Charanjit Aulakh
(74) *Attorney, Agent, or Firm* — White & Case LLP

(57) ABSTRACT

The present invention relates to a novel form of the (−)-enantiomer of 5-methoxy-2-[[(4-methoxy-3,5-dimethyl-2-pyridinyl)-methyl]sulfinyl]-1H-benzimidazole, i.e. S-omeprazole. More specifically, it relates to a novel form of the magnesium salt of the S-enantiomer of omeprazole trihydrate. The present invention also relates to processes for preparing such a form of the magnesium salt of S-omeprazole and pharmaceutical compositions containing it. Furthermore, the present invention also relates to new intermediates used in the process.

7 Claims, 5 Drawing Sheets

FORM OF S-OMEPRAZOLE

This application is a continuation of U.S. patent application Ser. No. 11/853,323, filed 11 Sep. 2007, now U.S. Pat. No. 7,745,466 which is a continuation of U.S. patent application Ser. No. 10/672,936, filed 25 Sep. 2003, now U.S. Pat. No. 7,411,070, which is a continuation of U.S. patent application Ser. No. 10/076,711, filed 14 Feb. 2002, now U.S. Pat. No. 6,677,455, which is a divisional of U.S. patent application Ser. No. 09/077,719, filed 8 Jun. 1998, now U.S. Pat. No. 6,369,085, which was the National. Stage of International Application No. PCT/SE98/00974, filed 25 May 1998.

FIELD OF THE INVENTION

The present invention relates to a novel form of the (−)-enantiomer of 5-methoxy-2-[[(4- methoxy-3,5-dimethyl-2-pyridinyl)-methyl]sulfinyl]-1H-benzimidazole, i.e. S-omeprazole. More specifically, it relates to a novel form of the magnesium salt of the S-enantiomer of omeprazole trihydrate. The present invention also relates to processes for preparing such a form of the magnesium salt of S-omeprazole and pharmaceutical compositions containing it. Furthermore, the present invention also relates to intermediates used in the process, and their preparation.

BACKGROUND OF THE INVENTION AND PRIOR ART

The compound 5-methoxy-2-[[(4-methoxy-3,5-dimethyl-2-pyridinyl)methyl]sulfinyl]-1H-benzimidazole, having the generic name omeprazole, and therapeutically acceptable salts thereof, are described in EP 5129. The specific alkaline salts of omeprazole are disclosed in EP 124 495. Omeprazole is a proton pump inhibitor, i.e. effective in inhibiting gastric acid secretion, and is useful as an antiulcer agent. In a more general sense, omeprazole may be used for prevention and treatment of gastric-acid related diseases in mammals and especially in man.

Omeprazole is a sulfoxide and a chiral compound, wherein the sulfur atom being the stereogenic center. Thus, omeprazole is a racemic mixture of its two single enantiomers, the R and S-enantiomer of omeprazole, herein referred to as R-omeprazole and S-omeprazole. The absolute configurations of the enantiomers of omeprazole have been determined by an X-ray study of an N-alkylated derivative of the (+)-enantiomer in non-salt form. The (+)-enantiomer of the non-salt form and the (−)-enantiomer of the non-salt form were found to have R and S configuration, respectively, and the (+)-enantiomer of the magnesium salt and the (−)-enantiomer of the magnesium salt were also found to have R and S configuration, respectively. The conditions for the optical rotation measurement for each of these enantiomers are described in WO 94/27988.

Certain salts of single enantiomers of omeprazole and their preparation are disclosed in WO 94/27988. These compounds have improved pharmacokinetic and metabolic properties which will give an improved therapeutic profile such as a lower degree of interindividual variation.

WO 96/02535 discloses a process for the preparation of the single enantiomers of omeprazole and salts thereof, and WO 96/01623 discloses a suitable tableted dosage forms of for instance magnesium salts of R- and S-omeprazole.

DESCRIPTION OF THE INVENTION

Figure 1:
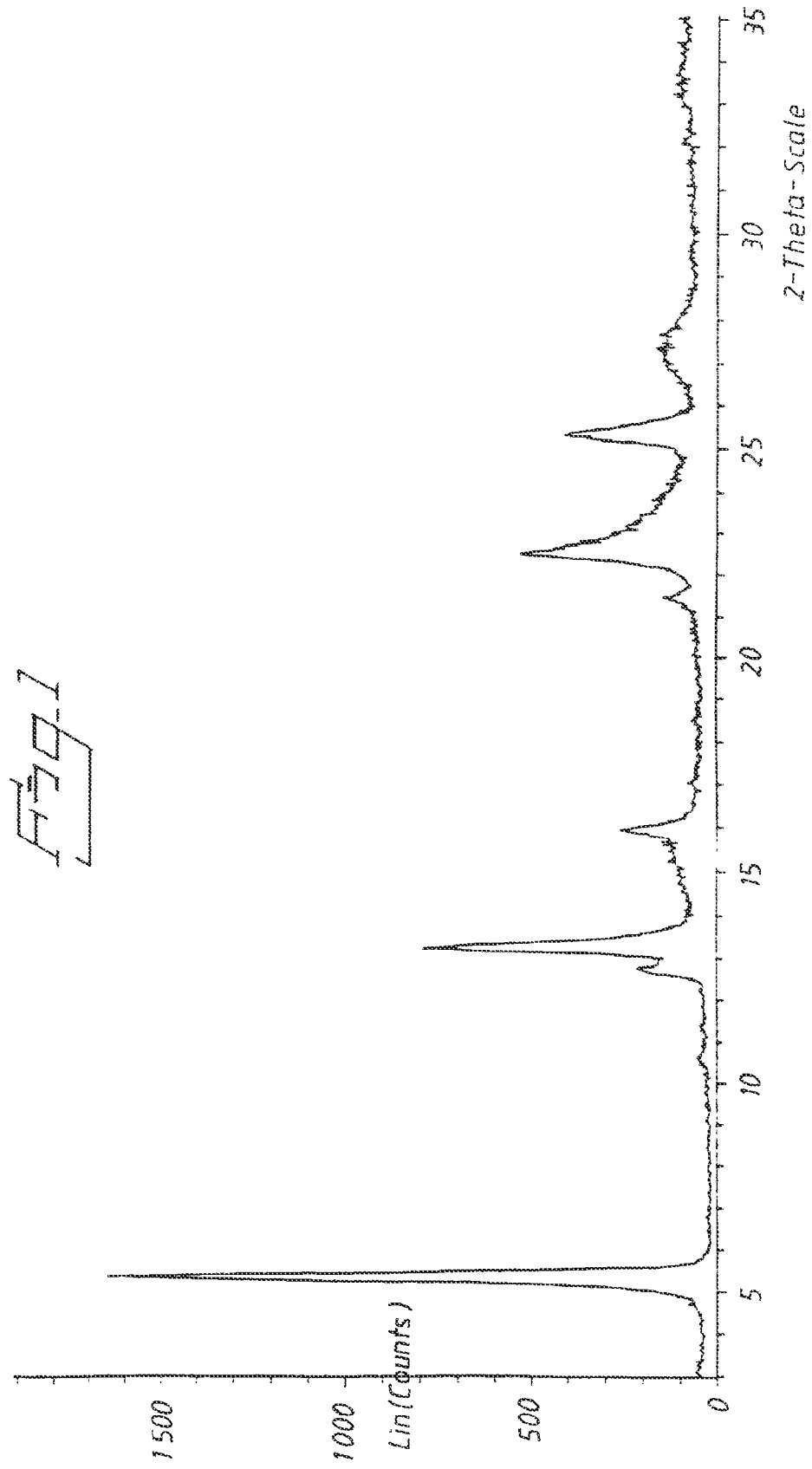
FIG. 1 shows a X-ray powder diffractogram of the magnesium salt of S-omeprazole trihydrate prepared according to the present invention.

It has surprisingly been found that the magnesium salt of S-omeprazole occurs in a number of structurally different forms. It is an object of the present invention to provide a substantially pure magnesium salt of S-omeprazole trihydrate, hereinafter referred to as the compound of the invention. This trihydrate can be obtained as a well defined compound. The present invention also provides a process to obtain and a method of differentiating the magnesium salt of S-omeprazole trihydrate from other forms of magnesium salts of S-omeprazole.

The compound of the invention is advantageous because it is more stable than the corresponding magnesium salt compounds in prior art and is therefore easier to handle and store. The compound of the invention is also easier to characterize because it exists in a well defined state. Additionally, the compound of the invention is easier to synthesize in a reproducible manner and thereby easier to handle in a full scale production.

The magnesium salt of S-omeprazole trihydrate obtained according to the present invention is substantially free from magnesium salts of R-omeprazole. The magnesium salt of S-omeprazole trihydrate obtained according to the present invention is also substantially free from other forms of magnesium salts of S-omeprazole, such as the corresponding magnesium salt compounds described in prior art, and dihydrates used in the preparation of the trihydrate compound according to the present invention.

The compound of the invention is characterized by the positions and intensities of the major peaks in the X-ray powder diffractogram, but may also be characterized by conventional FT-IR spectroscopy. These characteristics are not exhibited by any other form of magnesium salt of S-omeprazole and accordingly, the magnesium salt of S-omeprazole trihydrate is easily distinguishable from any other crystal form of the magnesium salt of S-omeprazole disclosed in prior art. The compound of the invention is characterized by being highly crystalline, i.e. having a higher crystallinity than any other form of magnesium salt of S-omeprazole disclosed in the prior art. With the expression "any other form" is meant anhydrates, hydrates, solvates, and polymorphs or amorphous forms thereof disclosed in the prior art. Examples of any other forms of magnesium salt of S-omeprazole includes, but are not limited to, anhydrates, monohydrates, dihydrates, sesquihydrates, trihydrates, alcoholates, such as methanolates and ethanolates, and polymorphs or amorphous forms thereof.

The compound of the invention may also be characterized by its unit cell.

In a further aspect, the present invention provides processes for the preparation of the magnesium salt of S-omeprazole trihydrate which comprises;

a) treating a magnesium salt of S-omeprazole of any form, for example prepared according to procedures known in the art such as Example A in WO 96/01623 which is incorporated herein by reference, with water at a suitable temperature for a suitable time. By a suitable temperature is meant a temperature which induces the transformation of starting material to product without decomposing any of these compounds. Examples of such suitable temperatures include, but are not limited to, room temperature and above. By a suitable time is meant a time that results in high conversion of the starting material into product without causing any decomposition of either compounds, i.e. results in a good yield. This suitable time will vary depending on the temperature, used in a way well known to people in the art. The higher the temperature, the shorter time is needed to give the desired conversion. The amount of water is not crucial and will depend on the process conditions used. The magnesium salt of S-omeprazole trihydrate is thereafter separated from the aqueous slurry, for example by filtration or centrifugation and thereafter dried to constant weight; or b) oxidizing 5-methoxy-2-[[(4-methoxy-3,5-dimethyl-2-pyridinyl)methyl]thio]-1H-benzimidazole, with an oxidizing agent and a chiral titanium complex, optionally in the presence of a base. The oxidation is carried out in an organic solvent, for example toluene or dichloromethane.

The crude product is converted to the corresponding potassium salt by treatment with a potassium source, such as methanolic potassium hydroxide or methanolic potassium methylate, followed by isolation of the formed salt.

The resulting potassium salt of S-omeprazole is thereafter converted to the corresponding magnesium salt by treatment with a magnesium source, such as magnesium sulfate in a lower alcohol, such as methanol. The solution is optionally filtered and the precipitation is initialized by addition of a non-solvent such as acetone. The product is filtered off and optionally washed with water and further processed as is described in a) above. Alternatively, the potassium salt may be treated with a magnesium source, such as magnesium sulfate in water, and isolation of the magnesium salt of S-omeprazole trihydrate, or any other conventional technique for transforming a potassium salt to the corresponding magnesium salt can be used and is within the scope of the present invention.

Yet a further aspect of the present invention is to provide a suitable intermediate used in the preparation of the compound of the invention, as well as a process for its preparation. The potassium salt of S-omeprazole is found to be such a suitable intermediate. The potassium salt of S-omeprazole may also be used as an active component of a pharmaceutical formulation to be used in the treatment of gastrointestinal diseases.

The compound of the invention, i.e. the magnesium salt of S-omeprazole trihydrate, prepared according to the present invention may be analyzed by XRPD, a technique which is known per se.

The amount of water in the magnesium salt of S-omeprazole trihydrate is determined by thermogravimetric analysis, a technique which is known per se.

The compound of the invention is effective as a gastric acid secretion inhibitor, and is useful as an antiulcer agent. In a more general sense, it can be used for prevention and treatment of gastric-acid related conditions in mammals and especially in man, including e.g. reflux esophagitis, gastritis, duodenitis, gastric ulcer and duodenal ulcer. Furthermore, it may be used for treatment of other gastrointestinal disorders where gastric acid inhibitory effect is desirable e.g. in patients on NSAID therapy, in patients with Non Ulcer Dyspepsia, in patients with symptomatic gastro-esophageal reflux disease, and in patients with gastrinomas. The compound of the invention may also be used in patients in intensive care situations, in patients with acute upper gastrointestinal bleeding, pre- and postoperatively to prevent aspiration of gastric acid and to prevent and treat stress ulceration. Further, the compound of the invention may be useful in the treatment of psoriasis as well as in the treatment of *Helicobacter* infections and diseases related to these. The compound of the invention may also be used for treatment of inflammatory conditions in mammals, including man.

Any suitable route of administration may be employed for providing the patient with an effective dosage of the magnesium salt of S-omeprazole trihydrate, according to the invention. For example, peroral or parental formulations and the like may be employed. Dosage forms include capsules, tablets, dispersions, suspensions and the like.

It is further provided a pharmaceutical composition comprising the magnesium salt of S-omeprazole trihydrate according to the invention, as active ingredient, in association with a pharmaceutically acceptable carrier, diluent or excipient and optionally other therapeutic ingredients. Compositions comprising other therapeutic ingredients are especially of interest in the treatment of *Helicobacter* infections. The invention also provides the use of the magnesium salt of S-omeprazole trihydrate of the invention in the manufacture of a medicament for use in the treatment of a gastric-acid related condition and a method of treating a gastric-acid related condition which method comprises administering to a subject suffering from said condition a therapeutically effective amount of the magnesium salt of S-omeprazole trihydrate according to the invention.

The compositions of the invention include compositions suitable for peroral or parental administration. The most preferred route is the oral route. The compositions may be conveniently presented in unit dosage forms, and prepared by any methods known in the art of pharmacy.

In the practice of the invention, the most suitable route of administration as well as the magnitude of a therapeutic dose of the magnesium salt of S-omeprazole trihydrate according to the invention in any given case will depend on the nature and severity of the disease to be treated. The dose, and dose frequency, may also vary according to the age, body weight, and response of the individual patient. Special requirements may be needed for patients having Zollinger-Ellison syndrome, such as a need for higher doses than the average patient. Children and patients with liver diseases generally will benefit from doses that are somewhat lower than the average. Thus, in some conditions it may be necessary to use doses outside the ranges stated below, for example long term treatments may request lower dosage. Such higher and lower doses are within the scope of the present invention. Such daily doses may vary between 5 mg to 300 mg.

In general, a suitable oral dosage form of the compound of the invention may cover a dose range from 5 mg to 300 mg total daily dose, administered in one single dose or equally divided doses. A preferred dosage range is from 10 mg to 80 mg.

The compound of the invention may be combined as the active component in intimate admixture with a pharmaceutical carrier according to conventional techniques, such as the oral formulations described in WO 96/01623 and EP 247 983, the disclosures of which are hereby incorporated as a whole by reference.

Combination preparations comprising the magnesium salt of S-omeprazole trihydrate and other active ingredients may also be used. Examples of such active ingredients include, but are not limited to anti-bacterial compounds, non-steroidal anti-inflammatory agents, antacid agents, alginates and pro-kinetic agents.

The examples which follow will further illustrate the preparation of the compound of the invention, according to different process routes and including new intermediates. These examples are not intended to limit the scope of the invention as defined hereinabove or as claimed below.

EXAMPLES

Example 1

S-5-methoxy-2-[[(4-methoxy-3,5-dimethyl-2-pyridinyl)-methyl]sulfinyl]-1H-benzimidazole magnesium salt trihydrate Water (157 kg) was added to the wet crystals of the magnesium salt of S-omeprazole, prepared according to Example 4, below. The mixture was heated to 38° C. with stirring and left for 3 hours. The crystals were filtered off and dried in vacuo. Yield: 31.6 kg X-ray powder diffraction analysis was performed on a sample of the crystals prepared above according to standard methods, which can be found in e.g. Kitaigorodsky, A. I. (1973), Molecular Crystals and Molecules, Academic Press, New York; Bunn, C. W. (1948), Chemical Crystallography, Clarendon Press, London; or Klug, H. P. & Alexander, L. E. (1974), X-Ray Diffraction Procedures, John Wiley and Sons, New York. The analysis gave the diffractogram depicted in FIG. 1. The main peaks, with positions and relative intensities, have been extracted from the diffractogram in FIG. 1 and is given below in table 1. The relative intensities are less reliable and instead of numerical values the following definitions are used.

| % Relative Intensity | Definition |
| --- | --- |
| 25-100 | vs (very strong) |
| 10-25 | s (strong) |
| 3-10 | m (medium) |
| 1-3 | w (weak) |
| <1 | vw (very weak) |

Some additional very weak peaks found in the diffractogram have been omitted from table 1.

TABLE 1

Positions and intensities of the major peaks in the XRP-diffractogram of the magnesium salt of S-omeprazole trihydrate.

| d-value/Å | Relative Intensity |
| --- | --- |
| 2.67 | m |
| 2.79 | m |
| 3.27 | m |
| 3.52 | s |
| 3.82 | s |
| 3.96 | vs |
| 4.14 | m |
| 5.2 | m |

TABLE 1-continued

Positions and intensities of the major peaks in the XRP-diffractogram of the magnesium salt of S-omeprazole trihydrate.

| d-value/Å | Relative Intensity |
| --- | --- |
| 5.6 | m |
| 6.7 | vs |
| 6.9 | s |
| 8.3 | w |
| 16.6 | vs |

Example 2

S-5-methoxy-2-[[(4-methoxy-3,5-dimethyl-2-pyridinyl)methyl]sulfinyl]-1H-benzimidazole potassium salt A solution of 5-methoxy-2-[[(4-methoxy-3,5-dimethyl-2-pyridinyl)methyl]thio]-1H-benzimidazole (15.4 g, 46.8 mmol) in toluene (70 ml) was heated to 50° C. and water (0.05 ml, 2.8 mmol) and D-(−)-diethyl tartrate (2.02 g, 9.82 mmol) were added. The reaction mixture was stirred for 20 minutes. Titanium(IV) isopropoxide 1.34 g, 4.68 mmol) was added and the reaction mixture was stirred for 45 minutes. The mixture was cooled to 30° C. and diisopropylethylamine (0.91 g, 7.01 mmol) was added followed by cumene hydroperoxide (9.52 g, 51.89 mmol). The resultant mixture was stirred at 30° C. for 3 hours. Methanol (40 ml) was added followed by potassium hydroxide (3.05 g, 46.8 mmol) in methanol (30 ml). Seed crystals were added and the reaction mixture was stirred at 35° C. overnight. The precipitated product was filtered off, washed with methanol and toluene and dried in vacuo. Yield: 9.74 g (54%).

Example 3

S-5-methoxy-2-[[(4-methoxy-3,5-dimethyl-2-pyridinyl)-methyl]sulfinyl]-1H-benzimidazole potassium salt Water (157.6 μl) was added to a solution of 5-methoxy-2-[[(4-methoxy-3,5-dimethyl-2-pyridinyl)methyl]thio]-1H-benzimidazole in toluene (370 ml; 211.5 g/l) with a water content of 0.031% (w/w), followed by addition of D-(−)-diethyl tartrate (8.55 ml). The solution was heated to 50° C. and stirred at this temperature for 20 minutes. Titanium(IV) isopropoxide (7.15 ml) was added and reaction was left at 50° C. for 45 minutes. The temperature was lowered to 30° C. and diisopropylethylamine (6.2 ml) was added. Cumene hydroperoxide was added at an appropriate speed to maintain the temperature from 28° C. to 34° C. The temperature was raised to 35° C. after 2 hours and potassium methoxide (24.55 g) in methanol (222 ml) was added. The mixture was filtered after 14 hours and the crystals were washed with methanol:toluene (240 ml; 1:1) and methanol (120 ml) and dried. Yield: 79 g (74%), ee>99.9%.

$[\alpha]_D^{20}$=+28.7° (c=1%, water); Assay: 89% is S-5-methoxy-2-[[(4-methoxy-3,5-dimethyl-2-pyridinyl)-methyl] sulfinyl]-1H-benzimidazole potassium salt (11% is methanol).

$^1$H-NMR (200 MHz, DMSO-d6, δ ppm): 2.23 (s, 3H), 2.24 (s, 3H), 3.71 (s, 3H), 3.75 (s, 3H), 4.40 (d, 1H), 4.78 (d, 1H), 6.58 (dd, 1H), 7.00 (d, 1H), 7.35 (d, 1H), 8.25 (s, 1H).

Figure 2:
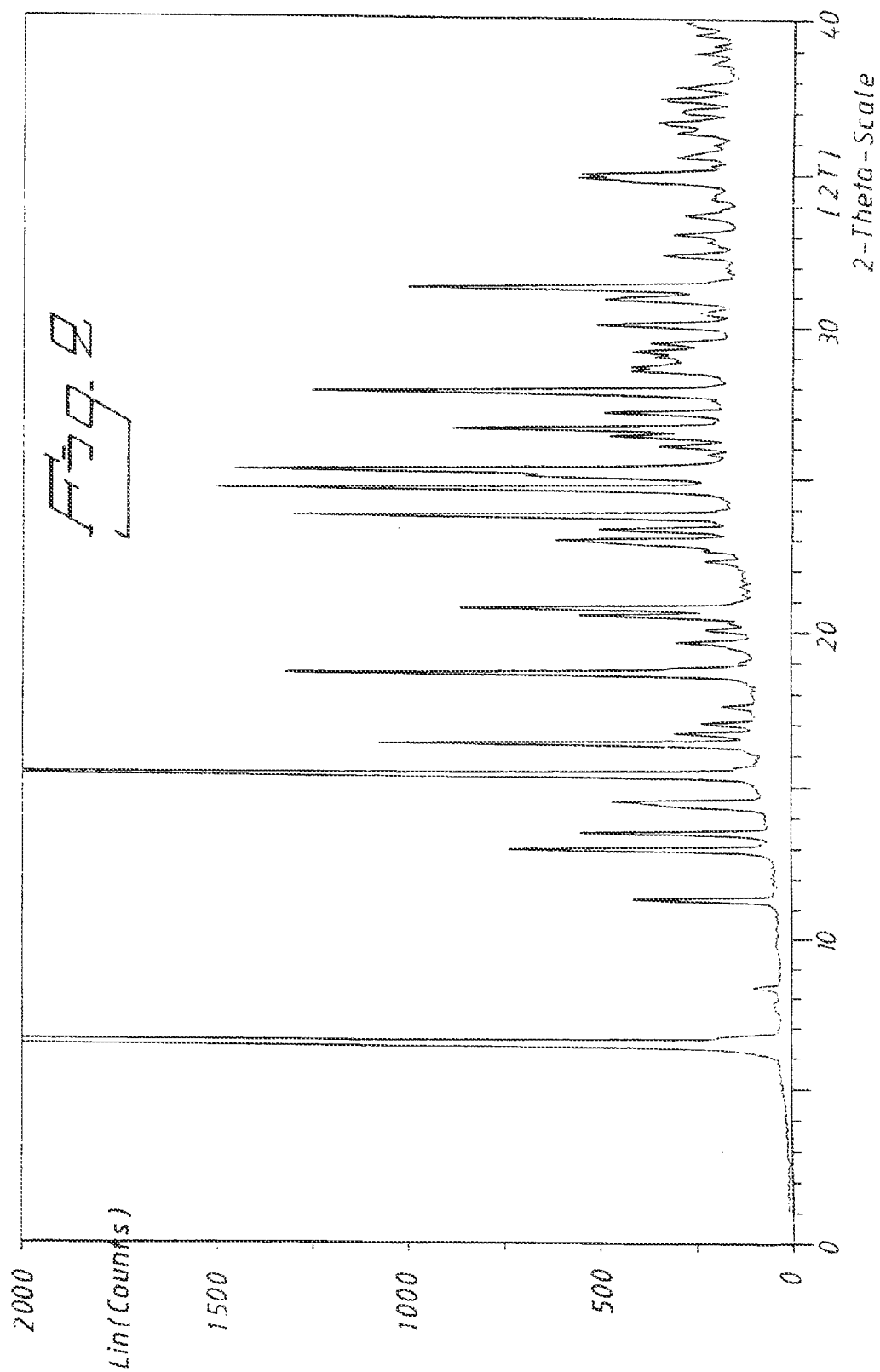
FIG. 2 shows a X-ray powder diffractogram of the potassium salt of S-omeprazole prepared and used in the present application (See examples 2 and 3)

The products from Examples 2 and 3 were analysed using X-ray powder diffraction as described in Example 1 and gave the diffractogram depicted in FIG. 2 and given below in Table 2. Some additional very weak peaks found in the diffractogram have been omitted from Table 2.

TABLE 2

Positions and intensities of the major peaks in the XRP-diffractogram of the potassium salt of S-omeprazole.

| d-value/Å | Relative intensity | d-value/ (Å) | Relative intensity |
|---|---|---|---|
| 13.6 | vs | 3.52 | m |
| 10.6 | vw | 3.42 | w |
| 7.8 | m | 3.38 | w |
| 6.8 | m | 3.34 | m |
| 6.5 | m | 3.28 | w |
| 6.2 | w | 3.20 | m |
| 6.1 | m | 3.12 | w |
| 5.8 | s | 3.06 | w |
| 5.4 | m | 3.03 | w |
| 5.3 | w | 2.97 | w |
| 5.2 | w | 2.93 | vw |
| 5.0 | vw | 2.89 | w |
| 4.75 | m | 2.85 | m |
| 4.71 | w | 2.76 | w |
| 4.52 | w | 2.71 | vw |
| 4.42 | w | 2.66 | vw |
| 4.32 | w | 2.58 | w |
| 4.27 | m | 2.57 | w |
| 3.98 | vw | 2.56 | w |
| 3.92 | w | 2.52 | vw |
| 3.89 | w | 2.47 | vw |
| 3.87 | w | 2.45 | vw |
| 3.81 | w | 2.43 | vw |
| 3.74 | m | 2.40 | vw |
| 3.60 | m | 2.38 | vw |
| 3.55 | m | 2.31 | vw |

$\alpha 1 = 1.54060 Å$

Example 4

S-5-methoxy-2[[(4-methoxy-3,5-dimethyl-2-pyridinyl)-methyl]sulfinyl]-1H-benzimidazole magnesium salt Methanol (148 kg) was added to S-5-methoxy-2-[[(4-methoxy-3,5-dimethyl-2-pyridinyl)-methyl]sulfinyl]-1H-benzimidazole potassium salt (71 kg, methanol content=13%). MgSO$_4$×7 H$_2$O (40 kg) was added to the mixture while stirring. After 70 minutes the mixture was filtered and the filtrate was washed with methanol (46 kg). The solution was concentrated to a volume of 100 liter, acetone (253 kg) was added and the resulting mixture was left for 4 hours. The precipitated product was filtered off, washed with acetone and water. The wet crystals were immediately used as is described in Example 1.

Example 5

S-5-methoxy-2-[[(4-methoxy-3,5-dimethyl-2-pyridinyl)-methyl]sulfinyl]-1H-benzimidazole magnesium salt dihydrate 5.0 g of the moist product from Example 4 with an approximate dry content of 74%, was dried in vacuum at 35° C. over night to yield 3.58 g (2.68 mmol) of S-5-methoxy-2-[[(4-methoxy-3,5-dimethyl-2-pyridinyl)-methyl]sulfinyl]-1H-benzimidazole magnesium salt dihydrate, named Form B.

Figure 3:
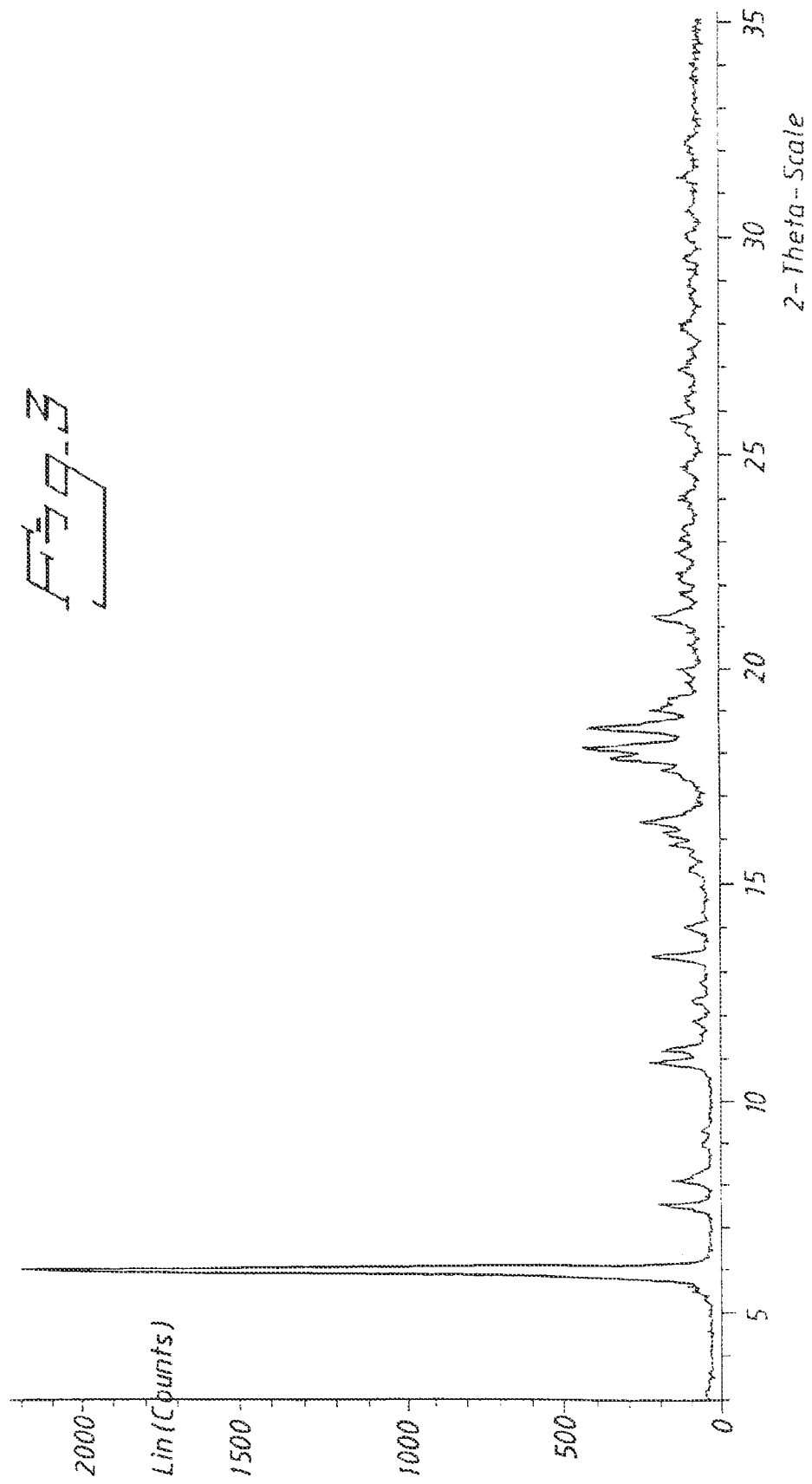
FIG. 3 shows a X-ray powder diffractogram of a magnesium salt of S-omeprazole dihydrate prepared and used in the present application (See example 5)

The product was analyzed using X-ray powder diffraction as described in Example 1, and the analyze gave the diffractogram depicted in FIG. 3 and given below in Table 3. Some additional peaks with low intensities found in the diffractogram have been omitted from Table 3.

TABLE 3

Positions and intensities of the major peaks in the XRP-diffractogram of the magnesium salt of S-omeprazole dihydrate, Form B.

| d-value/Å | Relative Intensity |
|---|---|
| 4.19 | m |
| 4.45 | m |
| 4.68 | m |
| 4.79 | s |
| 4.91 | s |
| 4.98 | s |
| 5.1 | m |
| 5.4 | s |
| 5.5 | m |
| 5.6 | m |
| 5.8 | m |
| 6.3 | m |
| 6.7 | s |
| 7.9 | m |
| 8.1 | s |
| 11.0 | m |
| 11.8 | m |
| 14.9 | vs |

Convertion of Magnesium Salt of S-Omeprazole Dihydrate to Trihydrate

This material was subsequently processed to S-5-methoxy-2-[[(4-methoxy-3,5-dimethyl-2-pyridinyl)-methyl]sulfinyl]-1H-benzimidazole magnesium salt trihydrate according to the procedure described for the moist substance in Example 1.

Example 6

S-5-methoxy-2-[[(4-methoxy-3,5-dimethyl-2-pyridinyl)-methyl]sulfinyl]-1H-benzimidazole magnesium salt dihydrate A methanolic solution of S-5-methoxy-2-[[(4-methoxy-3,5-dimethyl-2-pyridinyl)-methyl]sulfinyl]-1H-benzimidazole magnesium salt was prepared as is described in Example 4. Such a solution of S-5-methoxy-2-[[(4-methoxy-3,5-dimethyl-2-pyridinyl)-methyl]sulfinyl]-1H-benzimidazole magnesium salt (1.86 g) in 5 ml methanol was concentrated by evaporation until 1.58 ml methanol remained. Then, a mixture of 1.6 ml water and 6.32 ml aceton was added. The solution was allowed to crystallize during 26 h at room temperature. The resulting crystals were filtered off and dried at 40° C. under reduced pressure giving 1.17 g of S-5-methoxy-2-[[(4-methoxy-3,5-dimethyl-2-pyridinyl)-methyl]sulfinyl]-1H-benzimidazole magnesium salt dihydrate, named form A.

Figure 4:
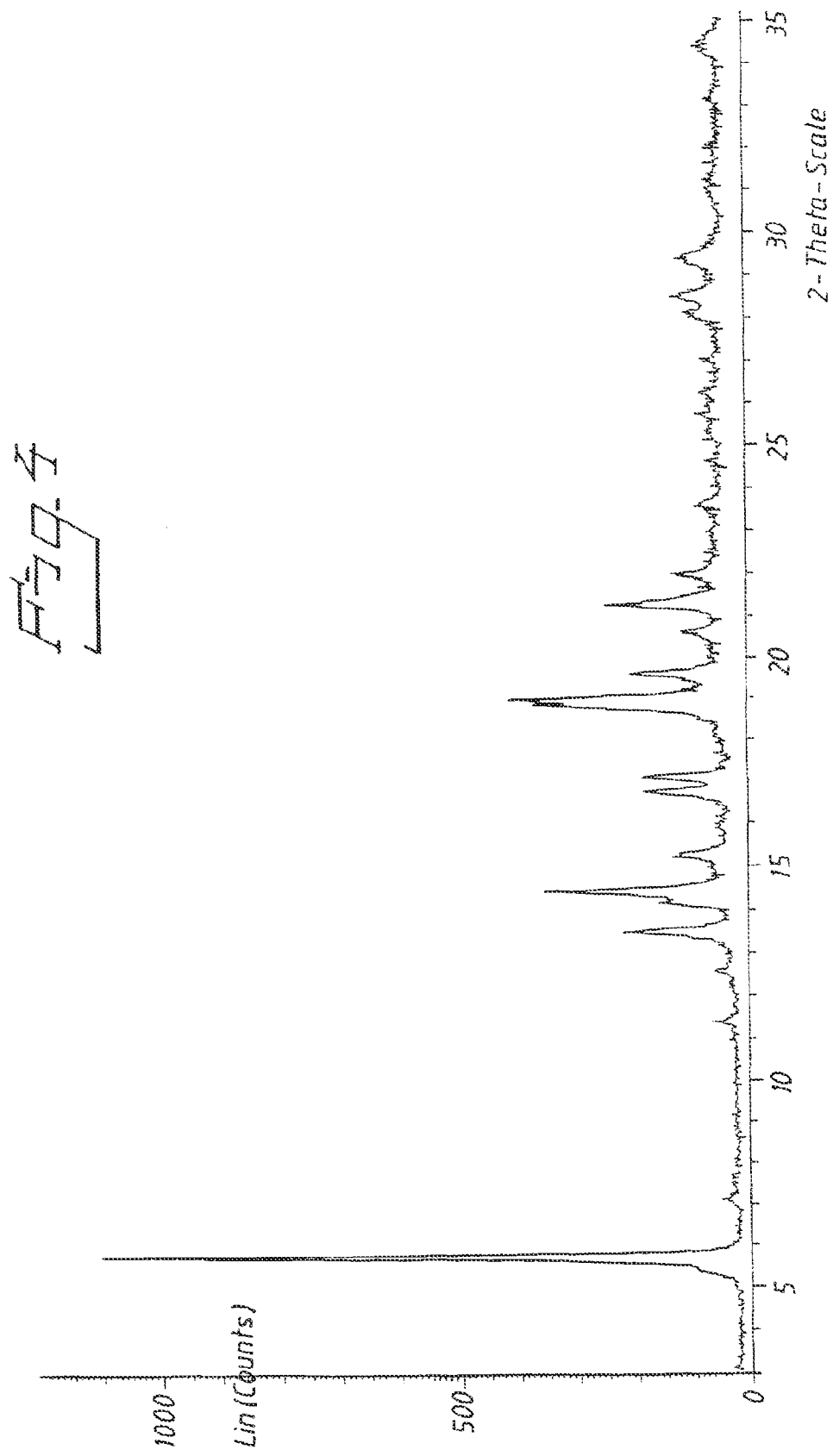
FIG. 4 shows a X-ray powder diffractogram of a magnesium salt of S-omeprazole dihydrate which is a polymorph of the dihydrate shown in FIG. 3 (See Example 6). This magnesium salt of S-omeprazole dihydrate has been prepared and can be used in the preparation of the magnesium salt of S-omeprazole trihydrate according to the present invention.

The product was analyzed using X-ray powder diffraction as described in Example 1 and gave the diffractogram depicted in FIG. 4 and given below in Table 4. Some additional peaks with low intensities found in the diffractogram have been omitted from Table 4.

TABLE 4

Positions and intensities of the major peaks in the XRP-diffractogram of the magnesium salt of S-omeprazole dihydrate, Form A.

| d-value/Å | Relative Intensity |
|---|---|
| 3.04 | s |
| 3.14 | s |
| 3.18 | m |
| 4.05 | s |

TABLE 4-continued

Positions and intensities of the major peaks in the XRP-diffractogram of the magnesium salt of S-omeprazole dihydrate, Form A.

| d-value/Å | Relative Intensity |
|---|---|
| 4.19 | s |
| 4.32 | m |
| 4.54 | s |
| 4.69 | vs |
| 5.2 | s |
| 5.3 | s |
| 5.8 | s |
| 6.2 | vs |
| 6.6 | s |
| 15.5 | vs |

Example 7

S-5-methoxy-2-[[(4-methoxy-3,5-dimethyl-2-pyridinyl)-methyl]sulfinyl]-1H-benzimidazole magnesium salt trihydrate 22.0 g (29.1 mmol) of S-5-methoxy-2-[[(4-methoxy-3,5-dimethyl-2-pyridinyl) methyl]sulfinyl]-1H-benzimidazole potassium salt was dissolved in 40 mL of water. The solution was seeded with 0.11 g (0.1 mmol) S-5-methoxy-2-[[(4-methoxy-3,5-dimethyl-2-pyridinyl)-methyl]sulfinyl]-1H-benzimidazole magnesium salt trihydrate. 22 mL (69.6 mmol) of $MgSO_4$ (aq) was added under a 3 h period. The slurry was filtered off and the precipitate was elutriated in water for approximately 30 minutes and the crystals were filtered off and dried (35° C., vacuum).

Yield: 9.15 g (11.6 mmol; 80%). The substance had a purity (HPLC):99.8 area %, Mg content: 3.40% (w/w) and ee: 99.8%.

The product was analyzed using X-ray powder diffraction and the result complies with FIG. 1 and Table 1.

Reference Example A

S-5-methoxy-2[[(4-methoxy-3,5-dimethyl-2-pyridinyl)-methyl]sulfinyl]-1H-benzimidazole magnesium salt (The method used is in accordance with the method described in Example A in WO 96/01623)

Magnesium (0.11 g, 4.5 mmol) was dissolved and reacted with methanol (50 ml) at 40° C. with a catalytic amount of methylene chloride. The reaction was run under nitrogen and was finished after five hours. At room temperature a mixture of the two enantiomers [90% (−)-isomer and 10% (+)-isomer] of 5-methoxy-2-[[(4-methoxy-3,5-dimethyl-2-pyridinyl)methyl]sulfinyl]-1H-benzimidazole (2.84 g, 8.2 mmol) was added to the magnesium methoxide solution. The mixture was stirred for 12 hours whereupon a small amount of water (0.1 ml) was added in order to precipitate inorganic magnesium salts. After 30 minutes stirring, these inorganic salts were filtered off and the solution was concentrated on a rotavapor. The residue was now a concentrated methanolic solution of the enantiomeric mixture (i.e. the title compound contaminated with the (+)-isomer), with an optical purity (enantiomeric excess, e.e.) of 80%. This mixture was diluted with acetone (100 ml) and after stirring at room temperature for 15 minutes, a white precipitate was obtained. Additional stirring for 15 minutes and thereafter filtration afforded 1.3 g (50%) of the title compound as white crystals. Chiral analyses of the crystals and mother liquor were performed by chromatography on an analytical chiral column. The optical purity of the crystals and mother liquor was found to be 98.4 e.e. and 64.4% e.e., respectively. Thus, the optical purity (e.e.) has been enhanced from 80% to 98.4% simply by crystallizing the Mg-salt from a mixture of acetone and methanol. The product was crystalline as shown by powder X-ray diffraction and the magnesium content was 3.44% as shown by atomic absorption spectroscopy. $[\alpha]_D^{20}=-131.5°$ (c=0.5%, methanol).

The product was analyzed using X-ray powder diffraction as described in Example 1 and gave the diffractogram depicted in FIG. 5 and given below in Table 5. Some additional very weak peaks found in the diffractograms have been omitted from Table 5.

TABLE 5

Figure 5:
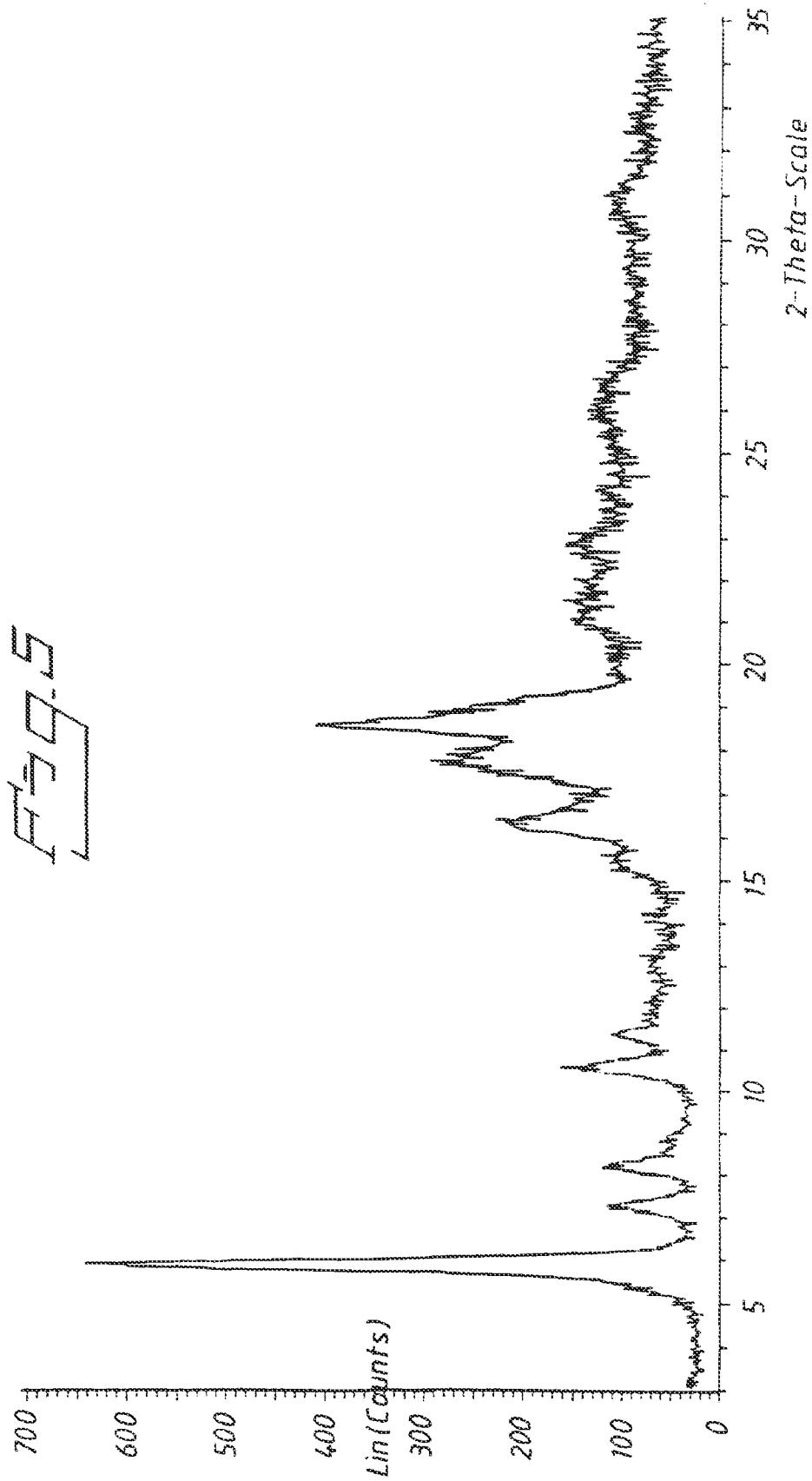
FIG. 5 shows X-ray powder diffractogram of the magnesium salt of S-omeprazole prepared according to example A in WO 96/01623.

Positions and intensities of the major peaks in the XRP-diffractogram shown in FIG. 5.

| d-value/Å | Relative Intensity |
|---|---|
| 2.90 | s |
| 3.41 | s |
| 3.90 | s |
| 4.13 | s |
| 4.79 | vs |
| 5.00 | vs |
| 5.4 | vs |
| 5.7 | s |
| 6.3 | s |
| 6.8 | s |
| 7.8 | s |
| 8.4 | vs |
| 10.8 | s |
| 12.2 | s |
| 15.1 | vs |

The invention claimed is:

1. A method of treating Helicobacter infections comprising the administration of an effective amount of a pharmaceutical composition comprising the magnesium salt of S-omeprazole trihydrate and an antibacterial compound to a patient in need thereof.

2. The method according to claim 1, wherein the magnesium salt of S-omeprazole trihydrate is represented by FIG. 1.

3. The method according to claim 1, wherein the magnesium salt of S-omeprazole trihydrate is characterized by the following peaks in its X-ray diffractogram:

| d-value/Å | Relative Intensity |
|---|---|
| 2.67 | M |
| 2.79 | M |
| 3.27 | M |
| 3.52 | S |
| 3.82 | S |
| 3.96 | Vs |
| 4.14 | M |
| 5.2 | M |
| 5.6 | M |
| 6.7 | Vs |
| 6.9 | S |
| 8.3 | W |
| 16.6 | Vs. |

4. The method according to claim 1, wherein the magnesium salt of S-omeprazole trihydrate is in a highly crystalline form.

5. The method according to claim 1, wherein the magnesium salt of S-omeprazole trihydrate is in a stable form.

6. The method according to claim 1, wherein the pharmaceutical composition is in unit dose form suitable for peroral or parenteral administration.

7. The method according to claim 1, wherein the total daily dose of the magnesium salt of S-omeprazole trihydrate is from 10 mg to 80 mg.

* * * * *